United States Patent [19]
Chen et al.

[11] Patent Number: 6,087,386
[45] Date of Patent: Jul. 11, 2000

[54] COMPOSITION OF ENALAPRIL AND LOSARTAN

[75] Inventors: Tzyy-Show H. Chen, Lansdale; Bassel Iskandarani, Lansdowne; Charles S. Sweet, Doylestown; Kenneth A. Krammer, Green Lane, all of Pa.; William Grossman, San Francisco, Calif.

[73] Assignee: Merck & Co., Inc., Rahway, N.J.

[21] Appl. No.: 08/877,742

[22] Filed: Jun. 17, 1997

Related U.S. Application Data

[60] Provisional application No. 60/020,301, Jun. 24, 1996.

[51] Int. Cl.[7] .......................... A61K 31/41; A61K 31/40
[52] U.S. Cl. ............................................. 514/381; 514/423
[58] Field of Search ...................... 514/381, 423

[56] References Cited

U.S. PATENT DOCUMENTS 5,266,583  11/1993  Ohtawa .................................. 514/381

FOREIGN PATENT DOCUMENTS 0 629 408 A1  12/1994  European Pat. Off. .
WO 91/17771  11/1991  WIPO .
WO 92/10097  6/1992  WIPO .

OTHER PUBLICATIONS

Makino et al., Hypertension (Dallas), 30(4), 796–802 (1997).

Stier et al., J. Hypertension 1993, 11(Suppl. 3): 537–542.

*Primary Examiner*—Phyllis G. Spivack
*Attorney, Agent, or Firm*—Valerie J. Camara; Mark R. Daniel

[57] ABSTRACT

The present invention discloses a pharmaceutical composition of enalapril and losartan and a pharmaceutically acceptable carrier.

5 Claims, 1 Drawing Sheet

COMPOSITION OF ENALAPRIL AND LOSARTAN

This application is a provisional of 60/020,301 filed Jun. 24, 1996.

BACKGROUND OF THE INVENTION

Angiotensin II (AII) is a potent vasoconstrictor. Its generation in the renin-angiotensin cascade results from the enzymatic action of renin on a blood plasma α2-globulin, angiotensinogen, to produce angiotensin I (AI). AI is then converted by angiotensin converting enzyme (ACE) to the octapeptide hormone AII. AII has been implicated as a causitive agent in hypertension. Therefore, ACE inhibitiors, which inhibit the production of AII via angiotensin converting enzyme, and AII receptor antagonists, which inhibit the function of AII, no matter the pathway of biosynthesis, are useful in the treatment of hypertension. The efficacy of these compounds in the treatment of heart failure is also being studied.

Pals, et al., Circulation Research, 29, 673 (1971) describe the introduction of a sarcosine residue in position 1 and alanine in position 8 of the endogenous vasoconstrictor hormone AII to yield an octapeptide that blocks the effects of AII on the blood pressure of pithed rats. This analog, [$Sar^1$, $Ala^8$] AII, initially called "P-113" and subsequently "saralasin," was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., Circulation Research, 29, 673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Some known non-peptide antihypertensive agents act by inhibiting an enzyme, called angiotensin converting enzyme (ACE), which is responsible for conversion of angiotensin I to AII. Captopril and enalapril are commercially available ACE inhibitors (ACEI's). Based on experimental and clinical evidence, about 40% of hypertensive patients are non-responsive to treatment with ACEI's. But when a diuretic such as furosemide or hydrochlorothiazide is given together with an ACEI, the blood pressure of most hypertensive patients is effectively normalized. Diuretic treatment converts the non-renin dependent state in regulating blood pressure to a renin-dependent state. Although AII antagonist compounds act by a different mechanism, i.e., by blocking the AII receptor rather than by inhibiting the angiotensin converting enzyme, both mechanisms involve interference with the renin-angiotensin cascade. A combination of the ACEI enalapril maleate and the diruetic hydrochlorothiazide is commercially available under the trademark Vaseretic® from Merck & Co. Publications which relate to the use of diuretics with ACEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Losartan potassium (losartan) represents the first antihypertensive in the class of AII receptor antagonists which is disclosed in a U.S. Pat. No. 5,138,069 issued on Aug. 11, 1992, and which is assigned to E. I. du Pont de Nemours. Losartan has been demonstrated to be a potent orally active AII antagonist, selective for the $AT_1$ receptor subtype useful in the treatment of hypertension.

Inhibition of the renin-angiotensin-aldosterone system (RAAS) with angiotensin converting enzyme (ACE) inhibitor and angiotensin II (AII) receptor antagonist therapy has also been shown to prevent and/or ameliorate renal disease of varying etiologies in animal models. Considering the differing pharmacodynamic effects of ACE inhibitors and AII receptor antagonists, i.e., ACE inhibitors (e.g. captopril, enalapril or lisinopril) inhibit the conversion of angiotensin I to angiotensin II and potentiate the effects of the kallikrein-kinin system whereas $AT_1$ selective AII receptor antagonists (e.g. losartan) selectively inhibit the function of AII at the receptor site, it is reasonable to suggest that an enhanced beneficial effect might be achieved through the coadministration of compounds from these therapeutic classes.

The coadministration of an ACE inihibitor with an AII antagonist for use in the treatment of experimental hypertension and congestive heart failure has been described in patent applications filed by SmithKline Beecham (WO 92/10097) and Pfizer (WO 91/17771). Additionally, a patent application filed by Merck and INSERM (EPO 629408) claims enhanced renal blood flow when treating with the combination. The instant invention discloses the combination of enalapril maleate and losartan potassium for use in the treatment of hypertension and congestive heart failure.

SUMMARY OF THE INVENTION

The present invention relates to a pharmaceutical composition of enalapril and losartan for use in the treatment of hypertension and heart failure. A method of treating hypertension and heart failure in a warm-blooded animal with a therapeutically effective dose amount of a pharmaceutical composition of an ACE inhibitor and an Angiotensin II receptor antagonist is disclosed. Included within the scope of the term pharmaceutical composition are a fixed dose combination and a concomitant therapy of a dose of enalapril and a dose of losartan. A bilayer or trilayer tablet dose form of the fixed dose enalapril-losartan combination comprising a first enalapril layer and a second losartan layer in the bilayer tablet dose form or in the trilayer tablet dose form an additional third layer of enalapril or excipient is also disclosed.

DETAILED DESCRIPTION OF THE INVENTION

Figure 1:
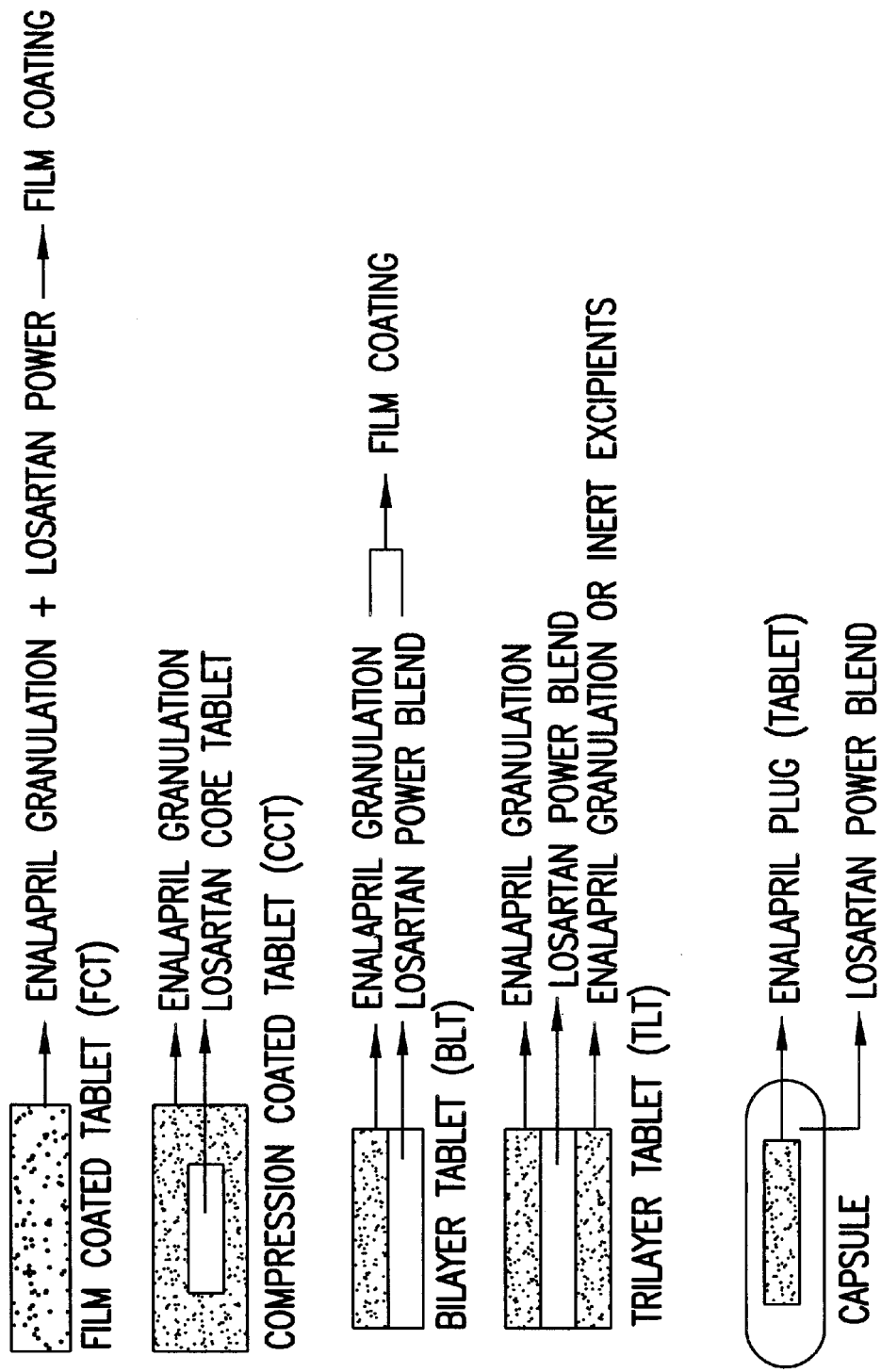
FIG. 1. Dosage forms for fixed combinations of enalapril maleate and losartan potassium, specifically, film coated tablet (FCT), compressed coated tablet (CCT), bilayer tablet (BLT), trilayer tablet (TLT), and capsule.

The present invention relates to a pharmaceutical composition of enalapril and losartan for the treatment of hypertension and heart failure. The present invention also relates to the method of treating hypertension and heart failure by coadministering to a mammal in need of such treatment a therapeutically effective amount of a pharmaceutical composition of enalapril and losartan or their pharmaceutically acceptable salts in a pharmaceutically acceptable carrier, with either concomitant therapy or a fixed combination of enalapril and losartan.

Concomitant therapy would include the sequential administration of members from the two classes of compounds. A fixed dose combination would be in the form of a tablet or capsule and comprises between 2.5 mg to about 20 mg of enalapril and 25 mg to about 50 mg of losartan and a pharmaceutical carrier. A preferred embodiment is a pharmaceutical composition consisting of about 10 mg enalapril maleate and 50 mg losartan potassium and a pharmaceutical carrier.

An additional embodiment of the invention is a bilayer or trilayer tablet dose form comprising a pharmaceutical composition of an enalapril maleate layer and a losartan potassium layer in a bilayer tablet or a first enalapril maleate layer, a second losartan potassium layer and a third layer of enalapril maleate or excipient in a trilayer tablet. The invention also includes a film coated bilayer or trilayer tablet dose form.

Enalapril maleate is the generic name for the compound: (S)-1-[N-(1-ethoxycarbonyl-3-phenylpropyl)-L-alanyl]-L-proline maleate. Enalapril maleate is currently being marketed in the United States under the tradename VASOTEC in a 2.5 mg, 5 mg, 10 mg and 20 mg dose and under the tradename VASERETIC as a combination with hydrochlorothiazide in a 5 mg/12.5 mg and a 10 mg/25 mg enalapril maleate/hydrochlorothiazide dose.

Also within the scope of this invention is the free acid form of enalapril maleate referred to by its generic name enalaprilat, having the chemical name, (S)-1-[N-(1-carboxyl-3-phenylpropyl)-L-alanyl]-L-proline dihydrate.

Losartan potassium is the generic name for the compound: 2-n-butyl-4-chloro-1-[(2'-(2H-tetrazol-5-yl)-1,1'-biphenyl-4-yl)methyl]-1H-imidazole-5-methanol. Losartan potassium is currently being marketed in the United States under the tradename COZAAR in a 25 mg and 50 mg dose and under the tradename HYZAAR as a combination with hydrochlorothiazide in a 50 mg losartan potassium/12.5 mg hydrochlorothiazide dose.

Also within the scope of this invention is the active metabolite of losartan, EXP3174, which also has the chemical name: 2-n-butyl-4-chloro-1-[(2'-(2H-tetrazol-5-yl)-1,1'-biphenyl-4-yl)methyl]-1H-imidazole-5-carboxylic acid.

Pharmaceutically suitable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. The preferred salts of this invention include, but are not limited to: potassium, sodium, calcium and ammonium salts of the ACE inhibitor and/or AII receptor antagonist.

Included within the scope of this invention is a method of treatment of hypertension and heart failure using pharmaceutical compositions comprising the ACE inhibitor, enalapril maleate and the AII antagonist, losartan potassium and a suitable pharmaceutical carrier.

DOSAGE FORMS

The pharmaceutical compositions of this invention can be administered for the treatment hypertension and heart failure according to the invention by any means that effects contact of the active ingredient compound with the site of action in the body of a warm-blooded animal. For example, administration can be parenteral, i.e., subcutaneous, intravenous, intramuscular or intra peritoneal.

Alternatively, or concurrently in some cases administration can be by the oral route.

The pharmaceutical compositions of this invention can be administered by any conventional means available for use in conjunction with pharmaceuticals. The pharmaceutical compositions can be administered alone, but are generally administered with a pharmaceutical carrier selected on the basis of the chosen route of administration and standard pharmaceutical practice.

For the purpose of this disclosure, a warm-blooded animal is a member of the animal kingdom which includes but is not limited to mammals and birds. The preferred mammal of this invention is human.

The dosage administered will be dependent on the age, health and weight of the recipient, the extent of disease, kind of concurrent treatment, if any, frequency of treatment and the nature of the effect desired. Usually, a daily dosage of the active ingredient compounds will be from about 2.5 mg to about 20 milligrams per day enalapril maleate and from about 25 mg to about 50 milligrams per day losartan potassium.

The active ingredients can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gyclols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium EDTA, sodium sulfite, citric acid and its salts or ascorbic acid, either alone or combined, are suitable stabilizing agents. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

Useful pharmaceutical dosage-forms for administration of the fixed combinations of this invention can be illustrated as follows (see Example 1):

CAPSULES

A large number of unit capsules are prepared by filling standard two-piece hard gelatin capsules each with a pharmacologically appropriate amount in milligrams of the powdered active ingredients:, 150 milligrams of lactose, 50 milligrams of cellulose, and 6 milligrams magnesium stearate.

An example of a capsule of 10 mg enalapril maleate/50 mg losartan potassium Combination:

| Ingredient | mg/tab |
|---|---|
| Enalapril/Losartan Strength | 10/50 |
| Losartan Core Tablet | |
| Losartan potassium | 50.00 |
| Microcrystalline Cellulose | 52.50 |
| Lactose, hydrous | 25.5 |
| Pregelatinized Starch | 20.95 |
| Magnesium Stearate | 1.05 |
| Total Wt of Losartan blend | 150.0 |
| Enalapril Maleate USP | 10.0 |
| Sodium Bicarbonate USP | 5.0** |
| Wt Allowance** | 1.4** |
| Lactose NF | 164.1 |
| Starch NF | 22.0 |
| Starch Pregelatinized NF | 2.2 |
| Red Ferric Oxide NF | 0.5 |
| Water Purified Usp | —* |
| Magnesium Stearate NF | 0.85 |
| Wt of Enalapril Plug (tablet) | 201.05 |
| #1 capsule | 76.0 |
| Total wt of the capsule | 427.05 |

*Evaporated during process of drying.
**Weight allowance due to neutralization with enalapril maleate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing a pharmacologically appropriate amount in milligrams of the active ingredient. The capsules are washed and dried.

TABLETS

A mixture of active ingredient and excipients are formulated into a tablet form. Appropriate coatings may be applied to increase palatability or delay absorption. Some examples on the combination tablets of this invention are:

1) Conventional film coated tablet (FCT) for 10 mg enalapril maleate/50 mg losartan potassium

| Ingredient | mg/tab |
|---|---|
| Core Tablet | |
| Enalapril Maleate | 10.0 |
| Sodium Bicarbonate USP | 2.5** |
| Weight Allowance** | 1.4** |
| Corn Starch NF | 20.0 |
| Lactose NF Hydrous 80 | 164.0 |
| Pregelatinized Starch NF 1551 | 2.0 |
| Magnesium Stearate NF | 1.5 |
| Losartan potassium | 50.0 |
| Microcrystalline Cellulose | 42.1 |
| Croscarmellose Sodium | 9.0 |
| Purified Water | 26.1* |
| Total Wt of Core Tablet | 300.0 |
| Hydroxypropyl Methylcellulose | 2.4 |
| Hydroxypropyl Cellulose NF | 2.4 |
| Titanium Dioxide USP | 0.96 |
| Water Purified | To 60 ul* |
| Total Wt of Film Coated Tablet | 306 |

**Weight allowance due to neutralization with enalapril maleate.
*Evaporated during process of drying.

2) Compression coated tablet (CCT or dry coated tablet) of 5/25, 10/25, 10/50, and 20/50 mg enalapril maleate/mg losartan potassium

| Ingredient | mg/tab | mg/tab | mg/tab | mg/tab |
|---|---|---|---|---|
| Enalapril/Losartan Strength | 5/25 | 10/25 | 10/50 | 20/50 |
| Losartan Core Tablet | | | | |
| Losartan potassium | 25.00 | 25.00 | 50.00 | 50.00 |
| Microcrystalline Cellulose | 26.25 | 26.25 | 52.50 | 52.50 |
| Lactose, hydrous | 12.75 | 12.75 | 25.5 | 25.5 |
| Pregelatinized Starch | 10.48 | 10.48 | 20.95 | 20.95 |
| Magnesium Stearate | 0.52 | 0.52 | 1.05 | 1.05 |
| Total Wt of Core Tablet | 75.0 | 75.0 | 150.0 | 150.0 |
| Enalapril Maleate USP | 5.0 | 10.0 | 10.0 | 20.0 |
| Sodium Bicarbonate USP | 2.5** | 5.0** | 5.0** | 10.0** |
| Wt Allowance** | 0.7 | 1.4 | 1.4 | 2.8 |
| Lactose NF | 198.1 | 164.1 | 396.2 | 328.2 |
| Starch NF | 22.8 | 22.0 | 45.6 | 44.0 |
| Starch Pregelatinized NF | 5.06 | 2.2 | 10.12 | 4.4 |
| Red Ferric Oxide NF | 0 | 0.5 | 0 | 1.0 |
| Water Purified Usp | —* | —* | —* | —* |
| Magnesium Stearate NF | 0.75 | 0.85 | 1.5 | 1.7 |
| Total Wt of Coated Tablet*** | 307.41 | 276.05 | 614.82 | 552.1 |

*Evaporated during process of drying.
**Weight allowance due to neutralization with enalapril maleate.
***10/50 uses twice of the amount of the Vasotec 5 mg granulation, 20/50 uses twice of the amount of the Vasotec 10 mg granulation.

3) Bilayer tablet (BLT) of 10 mg enalapril maleate/50 mg losartan potassium Combination:

| Ingredient | mg/tab |
|---|---|
| Enalapril/Losartan Strength | 10/50 |
| Losartan potassium | 50.00 |
| Microcrystalline Cellulose | 52.50 |
| Lactose, hydrous | 25.5 |
| Pregelatinized Starch | 20.95 |
| Magnesium Stearate | 1.05 |
| Total Wt of Losartan Layer | 150.0 |
| Enalapril Maleate USP | 10.0 |
| Sodium Bicarbonate USP | 5.0** |
| Wt Allowance** | 1.4** |
| Lactose NF | 164.1 |
| Starch NF | 22.0 |
| Starch Pregelatinized NF | 2.2 |
| Red Ferric Oxide NF | 0.5 |
| Water Purified Usp | —* |
| Magnesiurn Stearate NF | 0.85 |
| Wt of Enalapril Layer | 201.05 |
| Hydroxypropyl cellulose | 2.42 |
| Hydroxypropyl Methylcellulocose | 2.42 |
| Titanium Dioxide | 2.19 |
| Red Ferric Ocide NF | 0.088 |

-continued

| Ingredient | mg/tab |
|---|---|
| Talc USP | 0.88 |
| Total Tablet Weight | 359.05 |

*Evaporated during process of drying.
**Weight allowance due to neutralization with enalapril maleate.

4) Trilayer tablet (TLT) of 10/25, 10/50, and 20/50 mg enalapril/mg losartan Combination Tablet:

| Ingredient | mg/tab | mg/tab | mg/tab |
|---|---|---|---|
| Enalapril/Losartan Strength | 10/25 | 10/50 | 20/50 |
| Losartan powder blend | | | |
| Losartan potassium | 25.00 | 50.00 | 50.00 |
| Microcrystalline Cellulose | 26.25 | 52.50 | 52.50 |
| Lactose, hydrous | 12.75 | 25.5 | 25.5 |
| Pregelatinized Starch | 10.48 | 20.95 | 20.95 |
| Magnesium Stearate | 0.52 | 1.05 | 1.05 |
| Enalapril Granulation | | | |
| Enalapril Maleate USP | 10.0 | 10.0 | 20.0 |
| Sodium Bicarbonate USP | 5.0** | 5.0** | 10.0** |
| Wt Allowance** | 1.4 | 1.4 | 2.8 |
| Lactose NF | 164.1 | 396.2 | 328.2 |
| Starch NF | 22.0 | 45.6 | 44.0 |
| Starch Pregelatinized NF | 2.2 | 10.12 | 4.4 |
| Red Ferric Oxide NF | 0.5 | 0 | 1.0 |
| Water Purified Usp | —* | —* | —* |
| Magnesium Stearate NF | 0.85 | 1.5 | 1.7 |
| Total Wt of Tablet*** | 276.05 | 614.82 | 552.1 |

*Evaporated during process of drying.
**Weight allowance due to neutralization with enalapril maleate.
***10/50 uses twice of the amount of the enalapril maleate 5 mg granulation, 20/50 uses twice of the amount of the enalapril maleate 10 mg granulation.

Bilayer Tablets (BLT)

The BLT uses current losartan potassium powder blend and enalapril maleate granulation and applies a film coating process to mask the bitter taste from losartan. The bilayer tablet can be looked at as a modified conventional film coated tablet approach with less concern in segregation during scaling-up. Chemical stability of the bilayer tablet is expected to be better than or equal to the conventional film coated tablets and worse than or equal to the compression coated tablets due to the facts that: a) the contact surface area between enalapril maleate granulation and losartan potassium blend in the bilayer tablets is similar to that in the compression coated tablet (CCT) and much smaller than that in the film coated tablet (FCT); and b) the film coating process is required for the BLT and FCT but not for the CCT. The physical stability of the BLT is expected to be better than the CCT. BLT with barrel, triangle, round standard concave, and round deep curve shapes did not pose any friability concern when tumbled in a 36" coating pan with 50 kg dummy tablet load. Film coated round, 10/50 mg enalapril/losartan (E/L) bilayer tablets demonstrate acceptable dissolution results and meet the current specifications for VASOTEC and COZAAR.

Trilayer Tablet (TLT)

The trilayer tablet can be considered as a modified CCT with less concern of tablet physical/mechanical stability. The TLT uses current Vasotec granulation and possibly an inert excipient blend as the outer layers to sandwich the middle layer of losartan potassium powder blend. Though a taste testing will need to be conducted on the TLT, it is believed that the TLT may not need a film coating to mask the bitterness of losartan middle layer. The chemical stability of the TLT is expected to be similar to CCT and better than FCT and BLT. It is expected that the physical stability of the TLT is in between the CCT and film coated FCT and BLT.

INJECTABLE

A parenteral composition suitable for administration by injection is prepared by stirring a pharmacologically appropriate amount by weight of the active ingredients in 10% by volume propylene glycol. The solution is made to volume with water for injection and sterilized.

SUSPENSION

An aqueous suspension is prepared for oral administration so that each 5 milliliters contain a pharmacologically appropriate amount in milligrams of finely divided active ingredient, 100 milligrams of sodium carboxymethyl cellulose, 5 milligrams of sodium benzoate, 1.0 gram of sorbitol solution, U.S.P., and 0.025 milliliters of vanillin.

The same dosage forms can generally be used when enalapril and losartan are administered in a concomitant fashion. The above dosage forms and route of administration for a fixed combination of enalapril and losartan should be selected depending on the compatibility of the combined drugs. Suitable dosages, dosage forms and administration routes are illustrated in Tables A and B.

TABLE A

Examples of the doses of enalapril maleate that can be combined with losartan potassium which are useful for the treatment and/or prevention of hypertension and heart failure

| Drug | Dose (mg/day) | Formulation | Route of Admin. |
|---|---|---|---|
| enalapril maleate | 2.5, 5, 10, and 20 | Tablet/Capsule | Oral |

TABLE B

Examples of the doses of losartan that can be combined with enalapril for the treatment and/or prevention of hypertension and heart failure

| Drug | Dose (mg/day) | Formulation | Route of Admin |
|---|---|---|---|
| losartan potassium | 25, and 50 | Tablet/Capsule | Oral |

The following example further illustrate the method of treating hypertension and heart failure using a pharmaceutical composition including the active ingredients of the ACE inhibitor, enalapril maleate, and the AII receptor antagonist, losartan potassium, and as such are not to be considered or construed as limiting the invention recited in the appended claims.

A study was conducted examining the coadministration of 10 mg enalapril (ACE inhibitor) and 50 mg losartan ($AT_1$-selective AII receptor antagonist) as compared to the individual components. The study protocol is outlined below:

Study Design And Treatment Definition

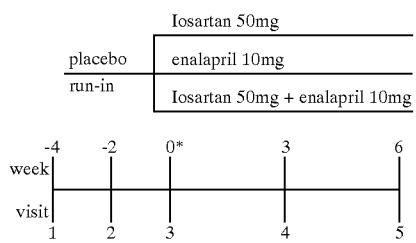

* Ambulatory blood pressure monitoring to be performed during the 24 hours preceeding the visit.

A. General

This is a randomized, double-blind, parallel, multicenter pilot study of 10 weeks duration. A 4-week placebo period will be followed by 6 weeks of double-blind treatment. Eligible hypertensive patients with a sitting diastolic blood pressure of 95–115 mmHg will enter a 4-week, single-blind, baseline placebo, pre-randomization period (the clinical team should not inform patients that they are in the placebo phase). Hypertensive patients whose SiDBP is 95–115 mmHg at the end of the Week -2 and Week 0 placebo baseline AND whose 24-hour ABPM mean DBP value at Week 0 is greater than or equal to 85 mmHg will be randomly assigned to 1 of 3 treatment groups: enalapril, losartan or concomitant therapy with losartan and enalapril. [See section for instructions on randomization procedures.] Patients will then take double-blind therapy for 6 weeks. No dose alterations should occur at any time, otherwise patients will be excluded from the study.

Approximately 45 patients will be randomized to each one of three groups for a total of 135 patients. Enrollment should be completed within 6 months. The study design and treatment groups of the double-blind portion of the study. A flowchart of the procedures and observations to be performed during the study (Prestudy—Week 6) is presented in the table below. Clinic Visits (Weeks -2 to 6) will occur between 0630 and 1100 hours. The visits may occur within a window of ±2 days of the scheduled date. Patients are to be in the fasted state on the days of scheduled laboratory tests (i.e., no food or liquids, except for water, are to be taken during the 8 hours prior to these clinic visits). Refer to the table below for a flow chart of the study visits.

B. Pre-Placebo Period

1. Clinical and Laboratory Procedures

At the first visit (week -4), the following procedures will be carried out:
   a. Obtain and review patient history.
   b. Explain the study and obtain informed consent.
   c. Perform a complete physical examination, including sitting and standing blood pressure and heart rate.
   d. Determine body weight.
   e. If the patient's prior history and laboratory tests are not available or known, draw blood for routine hematology and blood chemistry laboratory evaluation and perform urinalysis.
   f. Discontinue all antihypertensive medication according to the package circular.
   g. Perform a 12-lead ECG.
   IMPORTANT: Patients need to have an adequate antihypertensive drug-free period to ensure no carryover effects prior to placebo enrollment. Patients who have been off medication an insufficient time to meet the entry criteria will not be eligible for enrollment. For example, patients receiving ACE inhibitors and/or diuretics may require a longer drug-free period to establish their baseline blood pressure than patients taking calcium channel antagonists.

If a patient meets all entry criteria and has not been on any antihypertensive medications for at least 7 full days prior to the visit, the patient may enter the placebo baseline period immediately.

For patients requiring a tapering of previous antihypertensive medication, the placebo period will begin after the informed consent has been signed and the medication has been discontinued for a minimum of 7 full days. A second pre-placebo visit is necessary in order to ensure adequate washout. At the second visit, blood pressure will be assessed to ensure patient eligibility.

2. Patient Eligibility Assessment

Patients who meet the pre-placebo entry criteria based on their blood pressure (SiDBP 9.5–115 mmHg), medical history, body weight and the results of their physical examination, will be dispensed baseline medication (Bottles A and B).

C. Placebo Baseline Period: Weeks -4 to 0

1. Patient Identification

Eligible patients will be assigned temporary sequential baseline numbers in the order in which they enter the study.

2. Start of Placebo Therapy

Patients entering the placebo period will be started on 2 placebo tablets in the morning, one each from Bottles A and B labeled Weeks -4 to 0. The placebo tablets in Bottle A will be in the same image as losartan 50 mg and the placebo tablets in Bottles B will be in the same image as enalapril 10 mg. One tablet from each of Bottles A and B is to be taken orally within a 5-minute period once daily, between 0630 and 1100 hours for 4 weeks (Weeks -4 to 0). Patients will be instructed to start the medication on the following day between 0630 and 1100 hours.

3. Clinic Visits

Patients will be instructed to come to the clinic in a fasted state, on the day that laboratory tests are scheduled. They will also be told not to take any study medication on the morning of any scheduled visit but to bring all bottles of study drug with them to the clinic. Patients will take that day's medication from the bottles that are returned after the "trough" measurements are completed, except at the week 0 clinic visit, when they will take their medication from newly supplied bottles on that day.

4. Laboratory Screening Tests and 12-Lead Electrocardiogram (ECG)

A routine fasting blood chemistry, hematology analysis and urinalysis will be carried out at the pre-placebo visit if previous test results are not available. See the table below for a listing of the tests to be performed. These tests will be performed on all patients at Week -2. The results of the Week -2 laboratory screening tests will determine if the patient is eligible for entry into the double-blind period. If any clinically significant out of range values (Section VIII.B. specifies some of the laboratory parameters) or apparent abnormalities occur, the local laboratory testing will be repeated while the patient continues on placebo. If further laboratory measurements are not performed, or if the repeated values again indicate the patient is not an eligible candidate for this study, the patient will be immediately discontinued from the placebo period. Failure to repeat laboratory measurements when necessary will result in the patient being classified as a protocol violator.

At the pre-placebo clinic visit, an ECG will be obtained if one is not available within the previous 3 month period.

Screening and Safety Laboratory Tests

I. Hematology (Weeks −2 and 6*)
Hemoglobin
Hematocrit
WBC (total and differential)
Platelet Count II. Fasting Blood Chemistry (Weeks −2 and 6*)
Blood Urea
Creatinine
Total Bilirubin
SGOT (AST)
SGPT (ALT)
Alkaline Phosphatase
Glucose
Uric Acid
Total and HDL Cholesterol
Triglycerides
Sodium
Potassium III. Urinalysis by Dipstick (Weeks −2 and 6)
Protein
Glucose
Blood IV. Monthly Pregnancy Test (when applicable)
Central Laboratory Tests (Week 0 and Week 6) **
Blood Tests: Active Renin and Total Renin
Plasma Aldosterone
Plasma Cortisol
Plasma ACE Activity
Plasma Ang I and Plasma Ang II
Unrine Tests: 12-hour Unrinary Electrolytes 5. Blood Pressure (BP). Heart Rate (HR). and Body Weight
  a. "Trough" BP and Heart Rate (HR) Measurements
At all clinic visits, "trough" BP and HR measurements (sitting and standing) will be performed and recorded as described in Section XI.B.-D.
    Note: At the Week −4 and Week −2 clinic visits, "trough" SiDBP will be evaluated to determine patient eligibility for entry into the double-blind period as described in Section XI.B.2. Only patients who have a mean SiDBP of 95–115 mmHg at Week −4 and of 95–115 at Week −2 and Week 0 may continue in the study. In addition, mean 24-hour ABPM DBP must be ≧85 mmHg at Week 0.
  b. Body Weight
    Body weight will be obtained at all clinic visits.
6. Ambulatory Blood Pressure Measurements
Ambulatory BP monitoring will be performed on two occasions during the study (i.e., at week 0, or sooner for patients who enter the study early, and week 6). Spacelabs model #90207 (or equivalent) will be the ABP monitor used in this study. Procedures to be followed for all ABP monitorings are specified in section XI.B.3.

7. Early Entry into Double-Blind Treatment Period (Abbreviated Placebo Baseline Period)
As a safety precaution, a patient whose "trough" SiDBP is 106–115 mmHg at the end of the Week −2 clinic visit may be considered a candidate to enter the double-blind treatment period early. This patient must return to the clinic after at least 3 days have passed for another clinic evaluation. If, at this time, the mean "trough" SiDBP is again 106 to 115 mmHg, the patient may undergo the 24-hour ABPM without waiting for Week 0. If the mean 24 Hour ABPM DBP is ≧85 mmHg, the patient may be randomized to the double-blind treatment after all end-of-baseline measurements have been made.
  IMPORTANT: If the patient qualifies for early entry, all procedures scheduled for the Week 0 visit must be carried out at the second Week −2 visit. If the SiDBP at the second reading is lower than 106 mmHg, the patient will follow normal procedures, and will be re-evaluated at week 0.

D. Double-Blind Period: Weeks 1–6
  1. Patient Identification and Randomization
    At the Week 0 clinic visit (or Week −2 for patients meeting the early entry criteria), patients meeting all of the inclusion criteria and none of the exclusion criteria as described in Section VIII. A. and B., will be assigned an allocation number (AN) from a computer generated random allocation schedule. This AN will be used throughout the remainder of the study and will be placed on all patient workbooks and case report forms.
  2. Start of Double-Blind Treatment
    At the conclusion of the Week 0 measurements, 2 new study medication bottles for Weeks 1 to 6 will be dispensed. Bottle A will contain losartan 50 mg or placebo matching losartan; Bottle B will contain enalapril 10 mg or placebo matching enalapril. The patient will be instructed to take one tablet from each of Bottles A and B at the conclusion of the morning week 0 clinic visit and every subsequent morning between 0630 and 1100 hours within a maximum interval of 5 minutes. The time that the patient takes the first dose of active medication should be recorded and the patient should be instructed to return to the clinic 6 hours later for another blood pressure evaluation. The time that the patient returns should be recorded and blood pressure should be determined using the same method as in the other clinic visits (refer to Appendix IV).
  3. Clinic Evaluations: End of Weeks 3 and 6
    a. "Trough" BP and HR Measurements. ECG and Physical Exam
      At all clinic visits, "trough" BP and HR (sitting and standing) will be determined and recorded as described in Section XI.B.1&2.
      A "trough" ECG will be taken at the end of the Week 6 clinic visit as described in Section XI.G.3. A physical examination will be done at Week 6.
    b. Body Weight will be obtained at all clinic visits.
    c. Laboratory Assessment
      Blood will be collected for routine fasting hematology and blood chemistry at the Week 6 visits. Dipstick urinalysis will also be performed.

d. Clinical Assessment

An assessment of the patient's medical condition including adverse experiences will be performed at every visit.

E. Early Discontinuation From Study

1. Adverse Experiences

Provisions should be made for patients to telephone and/or return to the direct care of the investigator at any time should an unexpected change in their medical status develop during the study. Patients may withdraw at any time; they can be dropped from the study at the discretion of the investigator should any untoward effects occur. If a patient is discontinued prior to Week 6, the Week 6 schedule is to be followed for the final visit.

2. Inadequate BP Control

If, during the double-blind period (Weeks 1–6), the blood pressure is inadequately controlled (SiSBP >210 mmHg, or SiDBP >115 mmHg, or SiDBP increases by >15 mmHg from baseline (Week 0 reading) on two successive measurements separated by at least 3 days), the patient may, at the investigator's discretion, be discontinued from the study. Week 6 evaluations as listed in the study design table, must be performed on patients who are discontinued from the study prematurely. Any abnormalities in physical examination, laboratory, or other data must be followed by the investigator until resolved. All patients who do not meet the entry criteria will be considered protocol violators, including those among them who are discontinued due to lack of efficacy.

Concurrent Treatment

A. Diet

No change will be made in the patient's usual diet. Only on the day of scheduled laboratory tests will a patient be evaluated in the fasted state (i.e., no food or liquids, except for water, should be taken during the 8 hours prior to these clinic visits).

B. Drug Therapy

No drugs that may affect blood pressure, other than the study drugs, may be taken on a regular basis during the study. Other antihypertensive drugs are not to be taken during the study or during the 7 days prior to entry into the placebo baseline. Other investigational drugs may not be taken during this study.

In the event other medication is required on a short-term basis, e.g., antibiotic therapy, the name of the drug, indication for use, its dosage and dates of administration must be recorded in the workbooklet. Concomitant therapy that is unlikely to affect the blood pressure may be given. If in doubt, obtain approval of the Merck Clinical Monitor.

Clinical Techniques For Assessment Of Safety And Efficacy
Flowchart of Study Visits For
Losartan vs. Enalapril vs. Concomitant Therapy with
Losartan + Enalapril

|  | Pre-Placebo | Placebo | Base-line | Double-Blind Period |  |
|---|---|---|---|---|---|
| Visit: | 1 | 2 | 3 | 4 | 5 |
| Week: | −4 | −2 | 0 | 3 | 6 |
| Medical History |  |  |  |  |  |
| Sign Informed Consent |  |  |  |  |  |
| Complete Physical Examination |  |  |  |  |  |
| Weight |  |  |  |  |  |
| Clinic Visits[a] | b |  |  |  |  |
| Sitting & Standing BP & HR[c] | d,e | f | f |  |  |
| 24-hour ABPM |  |  | g |  | n |
| Laboratory Safety Tests[h,l] | i |  | j |  |  |
| ECG (12-lead) | k |  |  |  |  |
| Dispense Baseline Medications | e |  |  |  |  |
| Dispense Double-Blind Medication |  |  | m |  |  |
| Discontinue Double-Blind Medication |  |  |  |  |  |

[a]Clinic Visits (Weeks −2 to 6) will occur as indicated between 0630 and 1100 hours. The visits may occur within a window of ±2 days of the scheduled date. Patients are to be in the fasted state on the days of scheduled laboratory tests (i.e., no food or liquids, except for water, are to be taken during the 8 hours prior to these clinic visits).
[b]Patient must have been off all antihypertensive medication for ≧7 full days at the time of initial visit.
[c]Measurements are to be taken 24 hours (range 22 to 26 hours) after the last morning study dose.
[d]Mean SiDBP must be 95–115 mmHg or patient cannot begin the study.
[e]Only if patient is off antihypertensive medication at least 7 full days or patient must return for another evaluation when an adequate washout period is achieved (refer to section IX.B)
[f]Mean SiDBP must be 95–115 mmHg or patient cannot continue in study. The patient must return to the clinic 6 hours after taking the study drug at visit 3 (week 0) for an additional blood pressure measurement.
[g]The monitor is placed on day −1. 24-hour ABPM Mean DBP must be ≧85 mmHg or patient cannot be randomized to active treatment.
[h]Fasting hematology, blood chemistry and urinalysis as described in the table above.
[i]Perform tests unless previous test results are available.
[j]Repeat labs if necessary.
[k]An ECG will be taken if one is not available within the previous 3 month period.
[l]Pregnancy test for fertile women within 72 hours of the first double blind dose of test agent and monthly thereafter.
[m]First tablet of active treatment must be taken at the end of the clinic visit.
[n]The monitor is placed on the day before the clinic visit; and removed on the day of the clinicvisit.
NOTE: If a patient does not complete the study, all procedures scheduled for treatment Week 6 will be done on the day the patient discontinues treatment.

A. Blood Pressure Equipment

A standard mercury sphygmomanometer (maintained in good condition) will be used to measure trough blood pressure. An aneroid or a random zero sphygmomanometer (including the Hawksley device) or automated device may NOT BE USED.

B. Blood Pressure Measurement Techniques

1. Sitting and Standing Positions

Blood pressure will be measured in the sitting and standing positions at every clinic visit (baseline and treatment). Korotkoff Phase V will be used as the criterion for diastolic blood pressure. The proper cuff size should be used on the same arm throughout the study. The arm used for BP measurement will be the non-dominant arm, and will be recorded in the workbooklet. Blood pressure readings must be rounded to the closest mark (i.e., an even number). Odd numbers are not acceptable. If the reading falls exactly half-way between two marks, it should be rounded to the lower mark.

After at least 5 minutes of rest in the sitting position, BP will be measured at 1 minute intervals, at least 3 times until stability is obtained. To ensure stability of the blood pressure, none of the 3 consecutive SiDBP measurements may be greater than 5 mmHg from the calculated average of the 3 readings. For example, a patient with SiDBP readings of 102, 98 and 104 mmHg (mean 101 mmHg) would be acceptable. (All readings are within 5 mmHg of the mean). However, a patient with SiDBP readings of 100, 116 and 104 mmHg (mean 107 mmHg) would be unacceptable (the first two readings differ from the mean by 7 and 9 mmHg, respectively) and would require additional readings. This rule applies to sitting DBP only. The investigator will have to continue to take BP readings until a set of three consecutive acceptable SiDBP measurements have been obtained.

On the Blood Pressure Readings Worksheet (VS BP), record all sitting BP readings taken (systolic and diastolic), and calculate the average of each consecutive group of 3 readings. Transcribe only the sequence of 3 consecutive acceptable sitting BP readings (systolic and diastolic) onto the VS page of the workbooklet, in addition to the mean of the diastolic blood pressure values and the time the readings were taken.

Subsequently, after 2 minutes in the standing position, BP will be measured three times at one minute intervals. All 3 standing blood pressures (systolic and diastolic), in addition to the means, the time of the BP measurements and the time of the last study medication will be recorded in the workbooklet.

2. "Trough" BP Measurement

The routine BP measurement is a "trough" measurement; that is, the measurement is taken 24 hours (range 22 to 26 hrs) after the last morning drug dose. Sitting and standing BP measurements will be recorded exactly as described in Section XI.B.1. Trough measurements will be taken at each clinic visit.

The Week −4 SiDBP measurement must be 95–115 mmHg. The "trough" SiDBP measurement taken at the Week −2 and Week 0 clinic visits will be evaluated to determine patient eligibility into the double-blind phase of the study. In order to enter the double-blind treatment, SiDBP measurements at Week −2 and Week 0 must be 95–115 mmHg. In addition, the 24-hour mean DBP value at Week 0 must be >85 mmHg.

3. Ambulatory Blood Pressure Measurement

Ambulatory BP monitoring will be performed on two occasions during the study (i.e., at week 0 and week 6). Spacelabs model #90207 (or equivalent) will be the ABP monitor used in this study. For each monitoring, the ABP monitor will be programmed to take 3 readings/hour between 6:00 am and 9:59 p.m. ("awake" hours); 2 readings/hour will be taken between 10:00 p.m. and 5:59 a.m. ("asleep" hours). Procedures for all ABP monitorings are as follows:

Patients will report to the clinic on the day before their regular Week 0 and Week 6 visits. They will not have taken their medication that morning.

First, trough clinic blood pressure measurements will be performed using a mercury sphygmomanometer. These values will be used only to compare with the first 3 values from the monitor to verify satisfactory operation.

ABPM must be initiated immediately after trough clinic measurements.

The patient will be fitted with the ambulatory unit on the same arm as the "manual" BPs were measured.

The cuff selected depends upon the patients' arm circumference:

regular cuff: 24–32 cm large cuff: 32.1–42 cm

Three open (i.e., not blinded) readings are taken using the monitor and their mean is calculated. This mean must be within 5 mmHg of the mean calculated from the readings taken with the mercury sphygmomanometer. If the observed difference is greater than 5 mmHg, the procedure may be repeated. If the difference is still greater than 5 mmHg and there is no mechanical problem with the equipment, the patient cannot enter the study.

The patient is administered the study drug after the open (i.e., not blinded) readings on the ABP Monitor, and after the blinded monitoring period has been initiated.

ABPM must be no less than 24 hours (i.e., the 1 0 measurement cannot be considered complete unless data are available for at least a 24-hour period).

The following information is to be recorded in the workbook:

the manufacturer and model of the monitor to be used the 3 readings (Systolic and Diastolic) from the mercury sphygmomanometer, and their average the 3 readings (Systolic and Diastolic) from the monitor, and their average the time on the monitor for each verification reading the time the first ABP measurement the time of that day's dose the arm used for BP The patient will be asked to note the time he/she retires to bed that evening and awakes the next day. The patient will report to the clinic before taking the next morning's dose. He/she will come to the clinic at least 24 hours after ABPM initiation.

When the patient returns to the clinic, at least 24 hours later, (not having taken the study medication that morning):

The ABPM equipment will be removed.

All usual procedures for that visit will be performed, including trough clinic blood pressure measurements using a mercury sphygmomanometer. These values will be used for efficacy analysis in addition to ABPM data.

The time the patient went to sleep on the previous night and the time the patient awoke will be recorded.

The 24-hour ABPM mean systolic and diastolic blood pressures will be recorded.

After the completion of clinic visits at weeks 0, the patient will take the study medications from newly supplied bottles. At week 6, the same procedures will be followed, but no new study medication will be dispensed after the ABP monitor is removed.

The printout of BP readings from the ABP monitor will be considered the source document. A successful monitoring ensures that sufficient blood pressure readings have been obtained uniformly over the 24-hour period.

C. Timing of Dose and BP Measurements

Dosing Administration and Timing of BP Measurements

All medications must be taken at the same time each day during baseline and treatment periods (0630 to 1100 hours).

Only on the day of scheduled laboratory tests should the patients be in the fasted state. Patients must not eat or drink anything other than water during the 8 hours prior to these clinic visits.

All clinical evaluations must be done 24 hours (range 22 to 26 hours) after the last morning dose.

All values outside of the above defined window for dose administration or clinical evaluation will be considered protocol violations and the patient's visit will need to be repeated with the appropriate measurements within 3 days.

Patients will be instructed NOT to take their daily medication on the morning of their scheduled visit but to bring their bottles with them. Patients will be instructed to report the time they took the study medication on the previous day.

At each clinic visit, after all "trough" measurements have been taken, the drug will be administered from the set of bottles being returned to the clinic.

D. Heart Rate

The pulse rate, measured over at least 30 seconds, will be taken after 5 minutes in the sitting position and again after 2 minutes in the standing position. The pulse rate is to be taken at the beginning of each patient visit, prior to measuring the blood pressure. Any irregularities or significant changes in pulse from the previous visit must be documented with an ECG.

E. Medical History and Physical Examination

A complete physical examination will be performed at the initial pre-placebo baseline visit and Week 6 clinic visits or at the time of discontinuation. At entry into the study, as required by the case report forms, each patient's history will be recorded with emphasis placed on cardiovascular disease.

F. Body Weight

Body weight (in light indoor clothing without shoes) will be determined at the Baseline visit and each subsequent clinic visit. The patient must have an arm circumference <41 cm to enter the study.

G. Laboratory Screening and ECG

1. Routine Laboratory Testing

Complete laboratory evaluations will be performed at the Week −2 and 6 clinic visits or at the time of discontinuation. The results of the Week −2 laboratory screening tests will determine if the patient is eligible for entry into the double-blind phase of the study. These tests include fasting blood chemistry, hematology and urinalysis, and will be performed by each site's appointed laboratory (see the table above for a complete list of tests to be performed). A laboratory evaluation should be done at the pre-placebo visit unless the patient's laboratory values are available from tests carried out within the previous 2 week period.

Laboratory values outside of the established range of acceptance will be reassessed by repeating laboratory tests on specimens collected at an interim (non regularly scheduled) visit. If further laboratory measurements are not performed, or if the repeated values again indicate that the patient is not an eligible candidate for this study, the patient will be discontinued immediately from the placebo baseline period. Failure to repeat laboratory measurements when necessary will result in the patient being classified as a protocol violator.

2. ECG

A 12-lead electrocardiogram will be taken at the pre-placebo (if one is not available within the previous 3 month period) and week 6 clinic visit (or when the patient discontinues treatment) in the morning after the BP and HR measurements have been taken.

What is claimed is:

1. A pharmaceutical composition, wherein the pharmaceutical composition consists of an enalapril maleate layer and a losartan potassium layer in a bilayer tablet, the enalapril maleate layer containing enalapril maleate in a dose of about 2.5 mg to about 20 mg and the losartan potassium layer containing losartan potassium in a dose of about 25 mg to about 50 mg and a pharmaceutically acceptable carrier.

2. The pharmaceutical composition as recited in claim 1, wherein the bilayer tablet is film coated.

3. The pharmaceutical composition as recited in claim 2, wherein the pharmaceutical composition of the film coated, bilayer tablet consists of about 10 mg enalapril maleate in the enalapril layer and 50 mg losartan potassium in the losartan potassium layer.

4. A pharmaceutical composition, wherein the pharmaceutical composition consists of a trilayer tablet: a first enalapril maleate layer, a second layer of losartan potassium layer and a third enalapril maleate or an excipient layer, the first and third enalapril maleate layer containing a total dose of enalapril maleate of about 2.5 mg to about 20 mg and the second losartan potassium layer containing losartan potassium in a dose of about 25 mg to about 50 mg and a pharmaceutically acceptable carrier in each layer except where the third layer is an excipient layer.

5. The pharmaceutical composition as recited in claim 4, wherein the pharmaceutical composition of the trilayer tablet consists of:

(a) a total of about 10 mg enalapril maleate in the first and third enalapril maleate layers and 50 mg losartan potassium in the second losartan potassium layer, and (b) 10 mg enalapril maleate in the first enalapril layer, 50 mg losartan potassium in the second losartan potassium layer and excipients in the third excipient layer.

* * * * *